United States Patent
Martinez et al.

(10) Patent No.: US 11,524,176 B2
(45) Date of Patent: Dec. 13, 2022

(54) LOCATOR FOR PLACEMENT OF FIDUCIAL SUPPORT DEVICE METHOD

(71) Applicant: COWLES VENTURES, LLC, Spokane, WA (US)

(72) Inventors: Alvaro Martinez, Mercer Island, WA (US); Mary Ann Slavik, Mercer Island, WA (US); Emily Lin, Mercer Island, WA (US)

(73) Assignee: COWLES VENTURES, LLC, Spokane, WA (US)

( * ) Notice: Subject to any disclaimer, the term of this patent is extended or adjusted under 35 U.S.C. 154(b) by 0 days.

(21) Appl. No.: 16/801,104

(22) Filed: Feb. 25, 2020

(65) Prior Publication Data

US 2020/0289845 A1 Sep. 17, 2020

Related U.S. Application Data

(60) Provisional application No. 62/818,625, filed on Mar. 14, 2019.

(51) Int. Cl.
*A61N 5/10* (2006.01)

(52) U.S. Cl.
CPC .... *A61N 5/1001* (2013.01); *A61N 2005/1012* (2013.01); *A61N 2005/1023* (2013.01); *A61N 2005/1024* (2013.01)

(58) Field of Classification Search
CPC .......................................... A61N 5/1001–1027
See application file for complete search history.

(56) References Cited

U.S. PATENT DOCUMENTS

| | | |
|---|---|---|
| 3,351,049 A | 11/1967 | Lawrence |
| 3,566,125 A | 2/1971 | Linhart, Jr. et al. |
| 4,323,055 A | 4/1982 | Kubiatowicz |
| 4,349,033 A | 9/1982 | Eden |
| 4,401,124 A | 8/1983 | Guess et al. |
| 4,509,506 A | 4/1985 | Windorski et al. |
| 4,655,771 A | 4/1987 | Wallsten |
| 4,702,228 A | 10/1987 | Russell, Jr. et al. |
| 4,704,774 A | 11/1987 | Fujii et al. |
| 4,763,642 A | 8/1988 | Horowitz |
| 4,763,643 A | 8/1988 | Vrzalik |
| 4,805,628 A | 2/1989 | Fry et al. |
| 4,815,449 A | 3/1989 | Horowitz |

(Continued)

FOREIGN PATENT DOCUMENTS

| | | |
|---|---|---|
| CN | 101198287 A | 6/2008 |
| EP | 0292630 A1 | 11/1988 |
| JP | 2014504603 A | 2/2014 |
| KR | 20170037097 A | 4/2017 |
| WO | WO9533512 A1 | 12/1995 |

(Continued)

OTHER PUBLICATIONS

Pignol, M.D., "First Report of a Permanent Breast PD Seed Implant as Adjuvant Radiation Treatment for Early-Stage Breast Cancer"—Clinical Investigation 2006, 6 pages.

(Continued)

*Primary Examiner* — Thaddeus B Cox

(74) *Attorney, Agent, or Firm* — Manatt, Phelps & Phillips, LLP

(57) ABSTRACT

A locator for the placement of a fiducial support device for brachytherapy may be used to perform a brachytherapy treatment in which one or more radioactive seeds are implanted into a treatment region of a patient.

7 Claims, 5 Drawing Sheets

(56) References Cited

U.S. PATENT DOCUMENTS

| | | |
|---|---|---|
| 4,869,259 A | 9/1989 | Elkins |
| 4,954,126 A | 9/1990 | Wallsten |
| 4,977,897 A | 12/1990 | Hurwitz |
| 4,994,013 A | 2/1991 | Suthanthiran et al. |
| 4,995,396 A | 2/1991 | Inaba et al. |
| 5,014,708 A | 5/1991 | Hayashi et al. |
| 5,061,275 A | 10/1991 | Wallsten et al. |
| 5,076,278 A | 12/1991 | Vilkomerson et al. |
| 5,081,997 A | 1/1992 | Bosley, Jr. et al. |
| 5,163,896 A | 11/1992 | Suthanthiran et al. |
| 5,201,314 A | 4/1993 | Bosley et al. |
| 5,289,831 A | 3/1994 | Bosley |
| 5,327,891 A | 7/1994 | Rammler |
| 5,342,283 A | 8/1994 | Good |
| 5,460,592 A | 10/1995 | Langton et al. |
| 5,490,521 A | 2/1996 | Davis et al. |
| 5,503,614 A | 4/1996 | Liprie |
| 5,611,870 A | 3/1997 | Horne et al. |
| 5,622,687 A | 4/1997 | Krishnan et al. |
| 5,713,828 A | 2/1998 | Coniglione |
| 5,759,154 A | 6/1998 | Hoyns et al. |
| 5,766,135 A | 6/1998 | Terwilliger |
| 5,769,795 A | 6/1998 | Terwilliger |
| 5,808,020 A | 9/1998 | Ferrieri et al. |
| 5,820,549 A | 10/1998 | Marian, Jr. |
| 5,820,554 A | 10/1998 | Davis et al. |
| 5,821,541 A | 10/1998 | Turner |
| 5,833,593 A | 11/1998 | Liprie |
| 5,857,956 A | 1/1999 | Liprie |
| 5,861,226 A | 1/1999 | Home et al. |
| 5,921,933 A | 7/1999 | Sarkis et al. |
| 5,924,973 A | 7/1999 | Weinberger |
| 5,961,527 A | 10/1999 | Whitmore et al. |
| 5,961,529 A | 10/1999 | Arnold |
| 5,976,067 A | 11/1999 | Tucker et al. |
| 5,989,265 A | 11/1999 | Bouquet De La Joliniere et al. |
| 5,997,463 A | 12/1999 | Cutrer |
| 6,007,475 A | 12/1999 | Slater et al. |
| 6,010,445 A | 1/2000 | Armini et al. |
| 6,018,676 A | 1/2000 | Davis et al. |
| 6,030,333 A | 2/2000 | Sioshansi et al. |
| 6,045,495 A | 4/2000 | Weinberger |
| 6,045,775 A | 4/2000 | Ericcson et al. |
| 6,059,714 A | 5/2000 | Armini et al. |
| 6,060,036 A | 5/2000 | Armini |
| 6,060,040 A | 5/2000 | Tournier et al. |
| 6,066,083 A | 5/2000 | Slater et al. |
| 6,074,337 A | 6/2000 | Tucker et al. |
| 6,080,099 A | 6/2000 | Slater et al. |
| 6,086,942 A | 7/2000 | Carden, Jr. et al. |
| 6,095,967 A | 8/2000 | Black et al. |
| 6,099,457 A | 8/2000 | Good |
| 6,099,458 A | 8/2000 | Robertson |
| 6,103,295 A | 8/2000 | Chan et al. |
| 6,106,454 A | 8/2000 | Berg et al. |
| 6,106,473 A | 8/2000 | Violante et al. |
| 6,120,856 A | 9/2000 | Liberti et al. |
| 6,123,920 A | 9/2000 | Gunther et al. |
| 6,132,359 A | 10/2000 | Bolenbaugh |
| 6,132,677 A | 10/2000 | Ohriner |
| 6,139,819 A | 10/2000 | Unger et al. |
| 6,146,322 A | 11/2000 | Papirov et al. |
| 6,146,615 A | 11/2000 | Davies et al. |
| 6,159,142 A | 12/2000 | Alt |
| 6,174,330 B1 | 1/2001 | Stinson |
| 6,200,255 B1 | 3/2001 | Yu |
| 6,242,742 B1 | 6/2001 | Geay et al. |
| 6,242,743 B1 | 6/2001 | DeVito et al. |
| 6,347,443 B2 | 2/2002 | Coniglione |
| 6,364,855 B1 | 4/2002 | Zappala |
| 6,398,709 B1 | 6/2002 | Ehr et al. |
| 6,405,733 B1 | 6/2002 | Fogarty et al. |
| 6,508,786 B2 | 1/2003 | Huitema et al. |
| 6,547,782 B1 | 4/2003 | Taylor |
| 6,549,802 B2 | 4/2003 | Thornton |
| 6,572,525 B1 | 6/2003 | Yoshizumi |
| 6,579,262 B1 | 6/2003 | Mick et al. |
| 6,585,633 B2 | 7/2003 | Vitali et al. |
| 6,621,086 B1 | 9/2003 | Appleby |
| 6,648,811 B2 | 11/2003 | Sierocuk et al. |
| 6,723,052 B2 | 4/2004 | Mills |
| 6,752,753 B2 | 6/2004 | Hoskins et al. |
| 6,846,282 B1 | 1/2005 | Ford |
| 8,560,052 B2 | 10/2013 | Mills |
| 8,764,619 B2 | 7/2014 | Pitman |
| 10,449,387 B2 | 10/2019 | Pitman |
| 10,456,592 B2 | 10/2019 | Pitman |
| 2002/0022781 A1 | 2/2002 | McIntire et al. |
| 2002/0183581 A1 | 12/2002 | Yoe et al. |
| 2004/0059177 A1* | 3/2004 | Baltas .............. A61N 5/1007 600/3 |
| 2004/0116767 A1 | 6/2004 | Lebovic et al. |
| 2005/0049490 A1 | 3/2005 | Mills |
| 2005/0070753 A1 | 3/2005 | Forman et al. |
| 2006/0020199 A1* | 1/2006 | Stubbs .............. A61N 5/1014 600/411 |
| 2006/0100475 A1 | 5/2006 | White et al. |
| 2006/0122452 A1 | 6/2006 | Hooft |
| 2007/0021642 A1 | 1/2007 | Lamoureux et al. |
| 2007/0043291 A1 | 2/2007 | Fidel et al. |
| 2007/0049786 A1 | 3/2007 | Edmundson |
| 2007/0142695 A1 | 6/2007 | White et al. |
| 2007/0167749 A1 | 7/2007 | Yarnall et al. |
| 2007/0265486 A1 | 11/2007 | Van 't Hooft |
| 2007/0265487 A1 | 11/2007 | Lamoureux et al. |
| 2008/0086026 A1 | 4/2008 | Keppel et al. |
| 2009/0099402 A1 | 4/2009 | Lamoureux et al. |
| 2009/0198094 A1* | 8/2009 | Fenster .............. A61B 8/0841 600/3 |
| 2009/0228001 A1 | 9/2009 | Pacey |
| 2009/0264696 A1 | 10/2009 | White et al. |
| 2009/0326314 A1 | 12/2009 | Cutrer et al. |
| 2010/0036245 A1* | 2/2010 | Yu .............. A61N 5/1027 600/439 |
| 2010/0152519 A1 | 6/2010 | White et al. |
| 2010/0268014 A1* | 10/2010 | Pitman .............. A61N 5/1015 600/7 |
| 2011/0004094 A1 | 1/2011 | Stubbs et al. |
| 2012/0323117 A1 | 12/2012 | Neustadter et al. |
| 2013/0289389 A1 | 10/2013 | Hermann et al. |
| 2013/0289390 A1 | 10/2013 | Hermann et al. |
| 2014/0275984 A1 | 9/2014 | Hermann et al. |
| 2016/0022415 A1 | 1/2016 | Lebovic et al. |
| 2016/0051839 A1 | 2/2016 | Greskovich, Jr. et al. |
| 2017/0151033 A1 | 6/2017 | Faure |
| 2017/0181842 A1 | 6/2017 | Lebovic et al. |
| 2017/0181843 A1 | 6/2017 | Lebovic et al. |
| 2017/0296842 A1 | 10/2017 | Helle et al. |
| 2019/0336274 A1 | 11/2019 | Lebovic et al. |
| 2020/0276451 A1 | 9/2020 | Martinez et al. |
| 2020/0276455 A1 | 9/2020 | Martinez et al. |

FOREIGN PATENT DOCUMENTS

| | | |
|---|---|---|
| WO | WO9640352 A1 | 12/1996 |
| WO | WO9717104 A1 | 5/1997 |
| WO | WO9719706 A1 | 6/1997 |
| WO | WO9719724 A1 | 6/1997 |
| WO | WO9801186 A1 | 1/1998 |
| WO | WO9940970 A1 | 8/1999 |
| WO | WO0009211 A1 | 2/2000 |
| WO | WO0172202 A2 | 10/2001 |
| WO | WO2004014215 A2 | 2/2004 |
| WO | WO2007134103 A2 | 11/2007 |
| WO | WO2012100206 A2 | 7/2012 |

OTHER PUBLICATIONS

Cross MJ, et al. Impact of a Novel Bioabsorbable Implant on Radiation Treatment Planning for Breast Cancer. World J Surg. Feb. 2017, vol. 41, Issue 2, pp. 464-471.Published online Oct. 5, 2016 (Year: 2016).

(56) References Cited

OTHER PUBLICATIONS

Brown, Design Considerations for Piezoelectric Polymer Ultrasound Transducers, IEEE Trans on Ultrasonics, Ferro-electrics, and Frequency Control. vol. 47, No. 6, Nov. 2000, p. 1377-1396.
Dicker AP, Lin CC, Leeper DB, Waterman FM; "Isotope selection for permanent prostate implants? An evaluation of 103 Pd versus 125I based on radiobiological effectiveness and dosimetry," Seminars in Urologic Oncology, May 2000, 18(2):152-159. https://www.ncbi.nlm.nih.gov/pubmed/10875458.

* cited by examiner

LOCATOR FOR PLACEMENT OF FIDUCIAL SUPPORT DEVICE METHOD

RELATED APPLICATIONS

This application claims the benefit under 35 USC 119(e) to U.S. Provisional Application No. 62/818,625, filed Mar. 14, 2019, and which is incorporated herein by reference.

FIELD

The disclosure relates generally to a mechanism and method for radiation oncology.

BACKGROUND

When women are treated for breast cancer (which is the most commonly diagnosed cancer in women), they can opt for a mastectomy (complete removal of the breast tissue) or a breast conservation surgery. Due to the use of widespread screening mammograms, women are diagnosed with localized and early-stage disease so that the breast conservation surgery followed by radiation treatment may be used. The typical radiation treatment is adjuvant breast radiation. While the adjuvant breast radiation results in good survival rates, adjuvant breast radiation treatment typically takes 3.5 to 7 weeks which is too long. In addition, since the adjuvant breast radiation treatment is typically provided using external beam radiation, there is a greater risk of acute skin reactions due to the healthy tissue interaction with the radiation.

As a result, accelerated partial breast irradiation may be used which results in a quicker treatment time and less radiation-induced acute skin reactions. One technique used for the accelerated partial breast irradiation is brachytherapy. In one method, radioactive sources are permanently implanted into the breast tissue at the site of the surgery wherein the radioactive sources may be high dose or low dose.

Currently there are a handful of ways to insert radioactive sources into breast tissue. One technique is by a free hand method, another technique uses a compressive template device to temporary hold insertion catheters and the last technique uses a locking template system and non-fixated fiducial needle. These methods are limited in that they do not ensure the radioactive sources are placed in the desired location as prescribed by the treatment plan 100% of the time. The lack of ability to place the radioactive sources in the desired location means that the remaining tumor margin is not receiving the appropriate radiation and healthy tissue is receiving unwanted radiation.

In the high dose rate brachytherapy area, a clinician would place hollow catheters into the breast to facilitate the insertion of a temporary radioactive source per a treatment plan which are then removed once the treatment is completed. The placement of these catheters may be by either free hand directly into the breast or by free hand though compressive template systems used to stereo-tactically immobilize the breast. Both Varian Medical Systems and Nucletron offer commercially available template immobilization products.

In the low dose rate brachytherapy area, one method for permanent breast radioactive seed implantation is described in detail in "First Report of a Permanent Breast103PD Seed Implant As Adjuvant Radiation Treatment for Early-Stage Breast Cancer", Dr. Jean-Philippe Pignol et al., International Journal of Radiation Oncology Biological Physics, Vol. 64, No. 1, pp. 176-181 (2006) which is incorporated herein by reference. This method uses a non-fixated fiducial needle, locking template and stereotactic fixation to insert lose dose rate (LDR) radioactive source strands into the treatment site. In this method, the fiducial needle can be challenging to place in the surgical cavity because locating the surgical cavity relies on the user's ultrasound skills. Also, the fiducial needle can migrate/move once inserted thus changing the depth at which the source strands are deployed. In addition, the system is very cumbersome to use and is not user intuitive. The user manually operates the locking template and stereotactic fixation system by turning knobs to adjust and lock/unlock positions. The position and orientation of the locking template is determined by a treatment planning software. The correct position and orientation of the template are verified by other instruments such as an inclinometer and a ruler. Overall, the system can be difficult to use in a reproducible and precise manner.

Thus, it is desirable to provide a mechanism and method to facilitate the accurate placement of a fiducial support device into soft tissue, such as breast tissue and a method that utilizes this mechanism with the goal of improving the reproducibility of the procedure and ensuring that the sources are reliably and consistently inserted in an exact position per a patient prescription treatment plan from patient to patient as well as improve the ease-of-use of the device and procedure. It is to this end that the disclosure is directed.

DETAILED DESCRIPTION OF ONE OR MORE EMBODIMENTS

The following disclosure is particularly applicable to radioactive source implantation into breast tissue and it is in this context that the disclosure will be described. It will be appreciated, however, that the mechanism and method has greater utility since the mechanism can be used with other devices besides the template, needles, and radioactive sources and may be used to implant radioactive seeds/sources into various different types of tissues.

Figure 1:
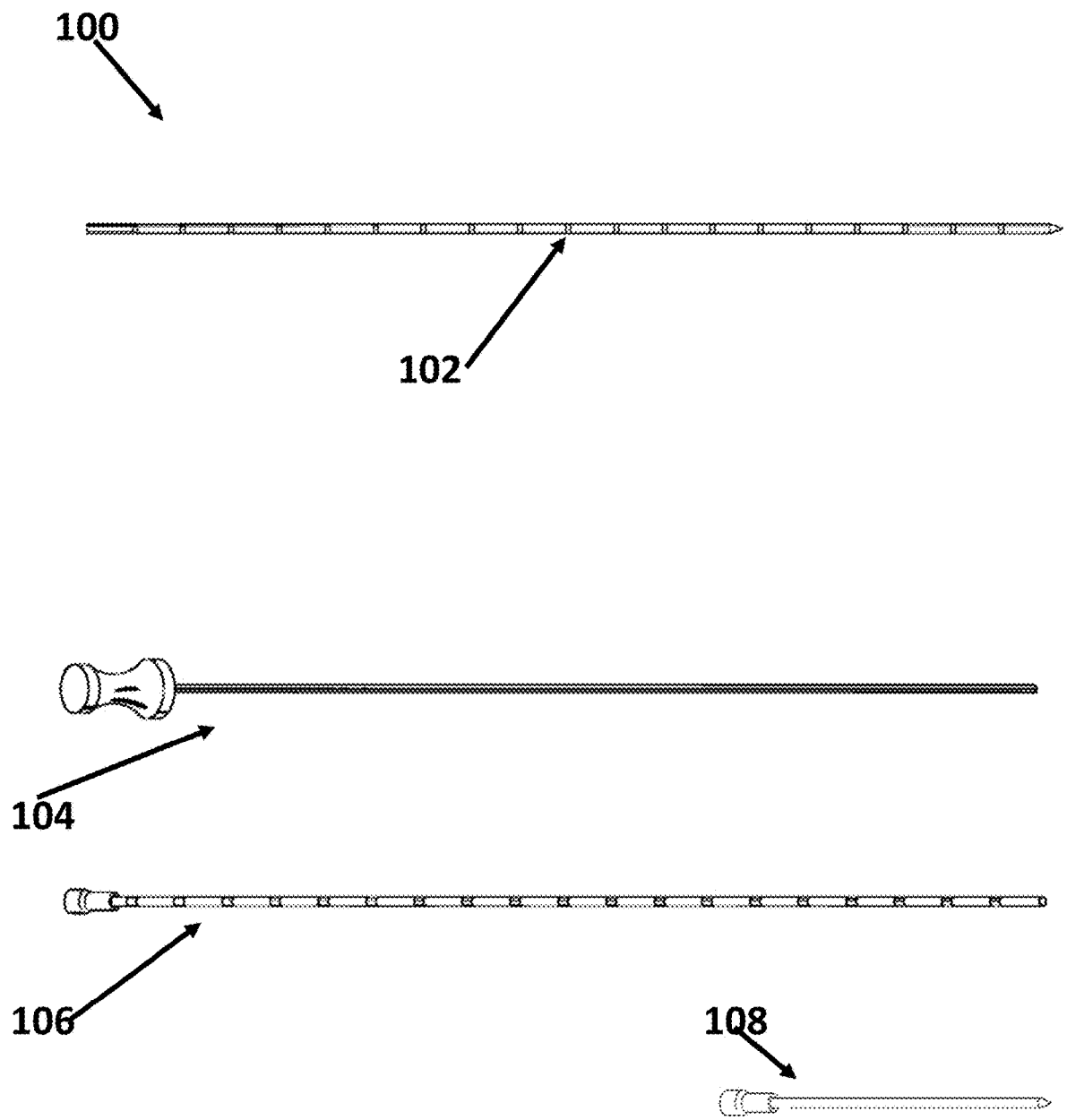
FIG. 1 illustrates an example a locator (needle guidance device) with accessory components that can be used with the mechanism.

FIG. 1 shows an example of a locator 100 with a sharpened tip for penetrating into the tissue to a treatment site of the patient. The locator 100 may be inserted into a treatment site (such as a lumpectomy cavity in one example) of the patient and then secured at the treatment site so that other medical devices, such as a fiducial needle in a brachytherapy treatment, may be precisely located adjacent, within or through the treatment site using the locator 100. In one embodiment, the locator 100 may be used to perform a brachytherapy procedure in which one or more radioactive seeds may be placed/implanted into position within the treatment site and the one or more radioactive seeds irradiate the tissue in/adjacent to the treatment site to, for example, kill any tumor cells that remain after a surgery to remove a tumor.

The locator 100 may have a body portion and may be a cannula, a guidewire, a catheter, a trocar with a tubular implant and/or a fiducial marker. The locator 100 may be manufactured out of any biocompatible materials, such as for example, a polymer-based material, stainless steel or a stainless steel alloy and/or bioabsorbable materials. The locator 100 may be visible under one or more imaging modalities (e.g., fluoroscopy, magnetic resonance imaging, computerized tomography, ultrasound, etc.) in which, for example, the entire body may be visible, features on or inside of it (i.e., beads, bands, markers, imaging agent) may be visible, balloon can be inflated for visibility and/or an accessory component that is visible under medical imaging can be placed inside the device. The accessory component may have features for depth measurements.

The locator 100 may also have an anchoring feature to secure the device in tissue and is easily removable. The anchoring feature may be, for example, a set of deployable hooks at one or both ends of the locator 100, a screw-like tip (tip has threads), a balloon that can be inflated and/or a surface or holes for suturing. The locator 100 may be placed surgically or percutaneously into the treatment site may have, for example, a sharpened tip to facilitate easy penetration into tissue although the locator device 100 can only pierce through tissue with a rigid stylet inside it since, without the rigid stylet, the locator device 100 is flexible and/or have an accessory component such as a trochar. The locator 100 may be placed optimally using output from imaging software or treatment planning software.

The locator 100 also may have one or more periodic markers 102 for depth measurements that may be used as the locator for placement of a fiducial support device. The locator 100 may include one or more accessory components. For example, the accessory components may include a stylet 104, a fiducial marker 106 and/or a obturator cap 108, that may be used with the locator.

Figure 2:
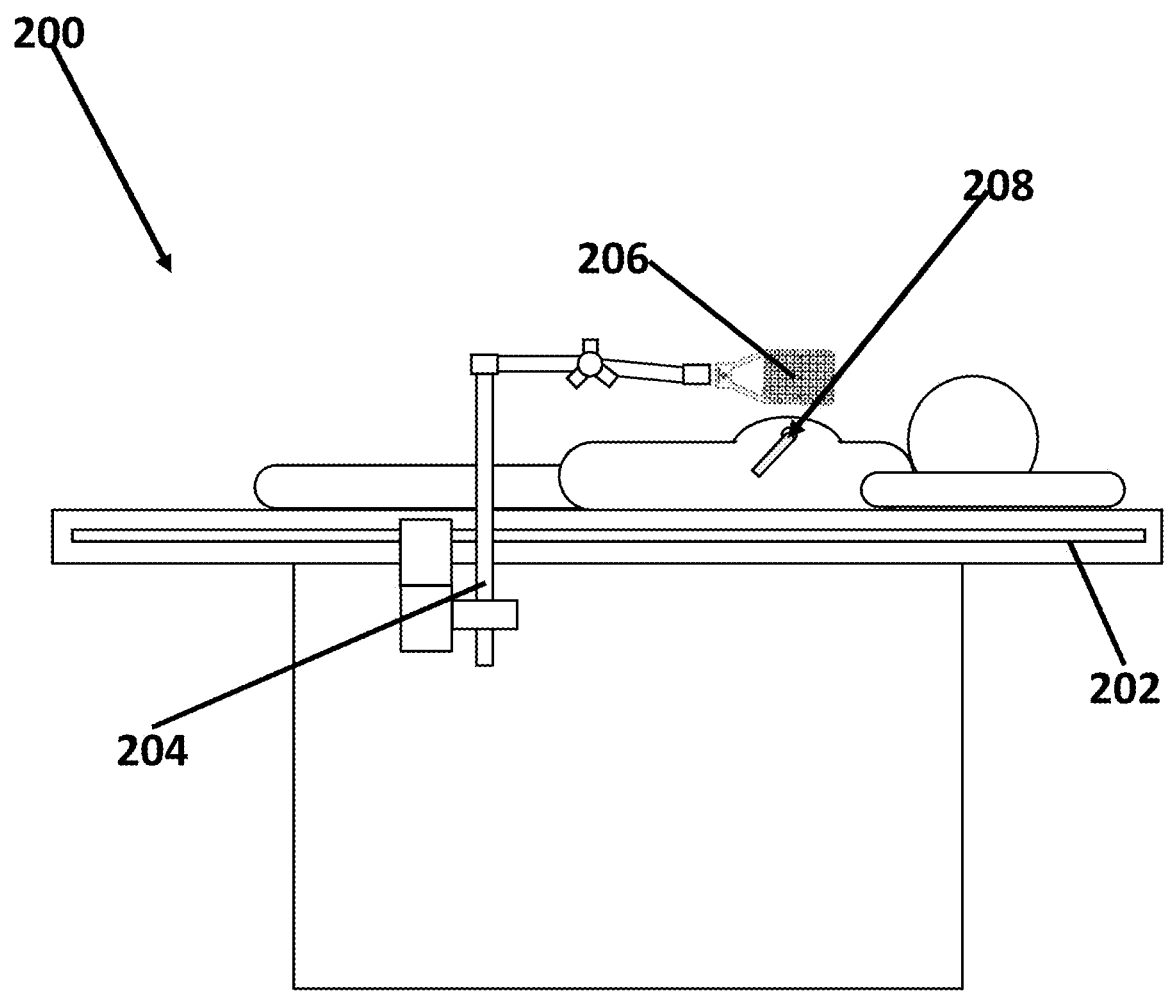
FIG. 2 illustrates an example of a method for facilitating the placement of a fiducial needle with a locator that is a cannula (needle guidance device)

FIG. 2 shows a brachytherapy system 200 that fixedly attaches to a rail on an operating room table 202 to fix a template 206 adjacent a patient who is undergoing brachytherapy breast cancer treatment in the example shown in FIG. 2. As shown in FIG. 2, the brachytherapy system 200 can include, for example, the orientable brachytherapy template 206, one or more stereotactic armatures 204 that position the template 206 related to the table 202 and can lock the position of the template 206 relative to the table 202 once the template is positioned correctly adjacent the treatment site of the patient. The brachytherapy system 200 also may have an automatic needle insertion system that inserts the needles with the radioactive sources/seeds into the patient using the locator 100. During the treatment, a fiducial needle 208 may be inserted into a cannula (the locator or needle guidance device 100) into the breast tissue for placement of the fiducial needle so that radioactive sources may be inserted into the breast tissue.

Figure 3:
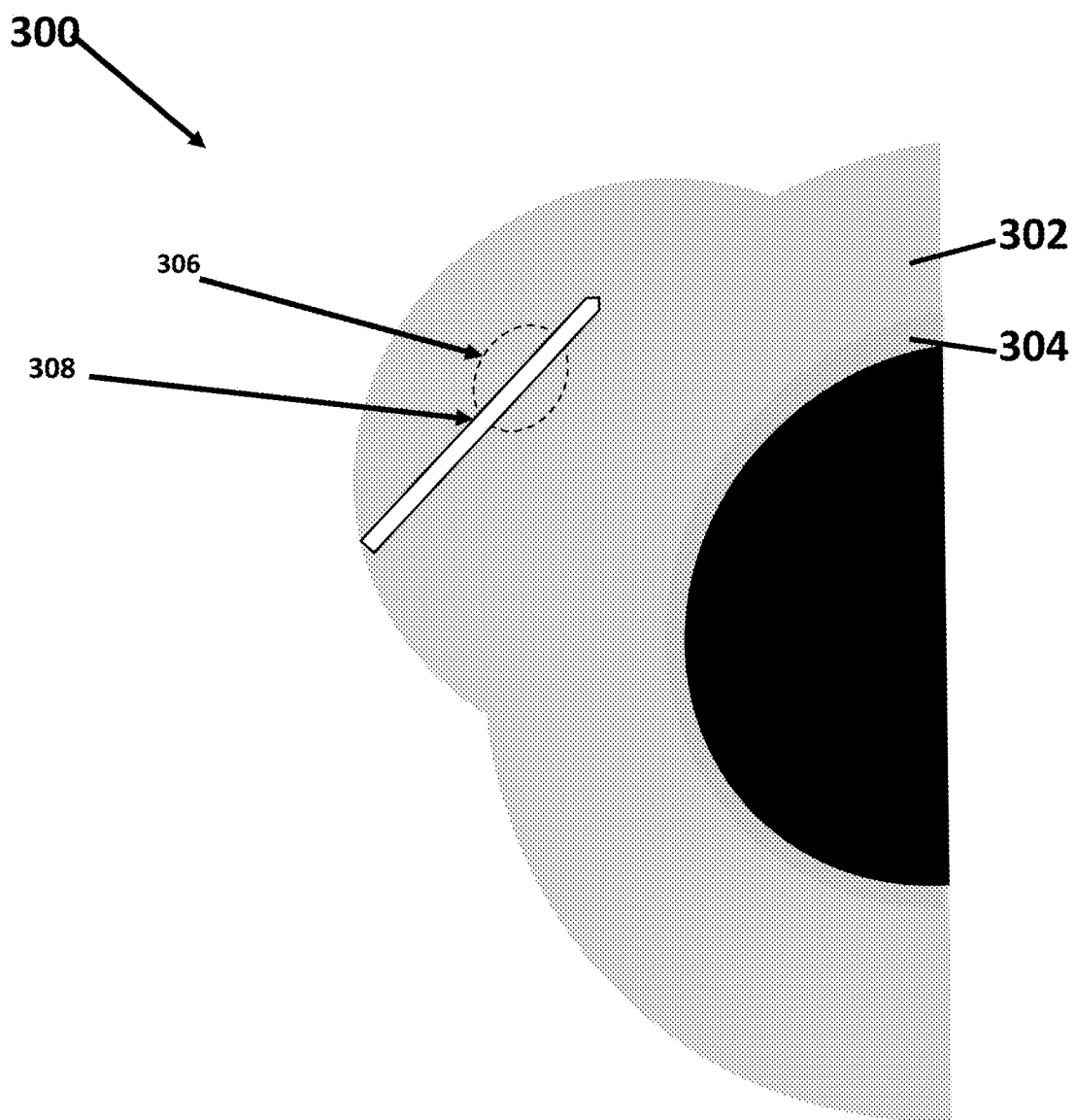
FIG. 3 illustrates a view of a breast with a cavity after the surgical removal of the tumor and a locator (needle guidance device) is implanted.
Figure 4:
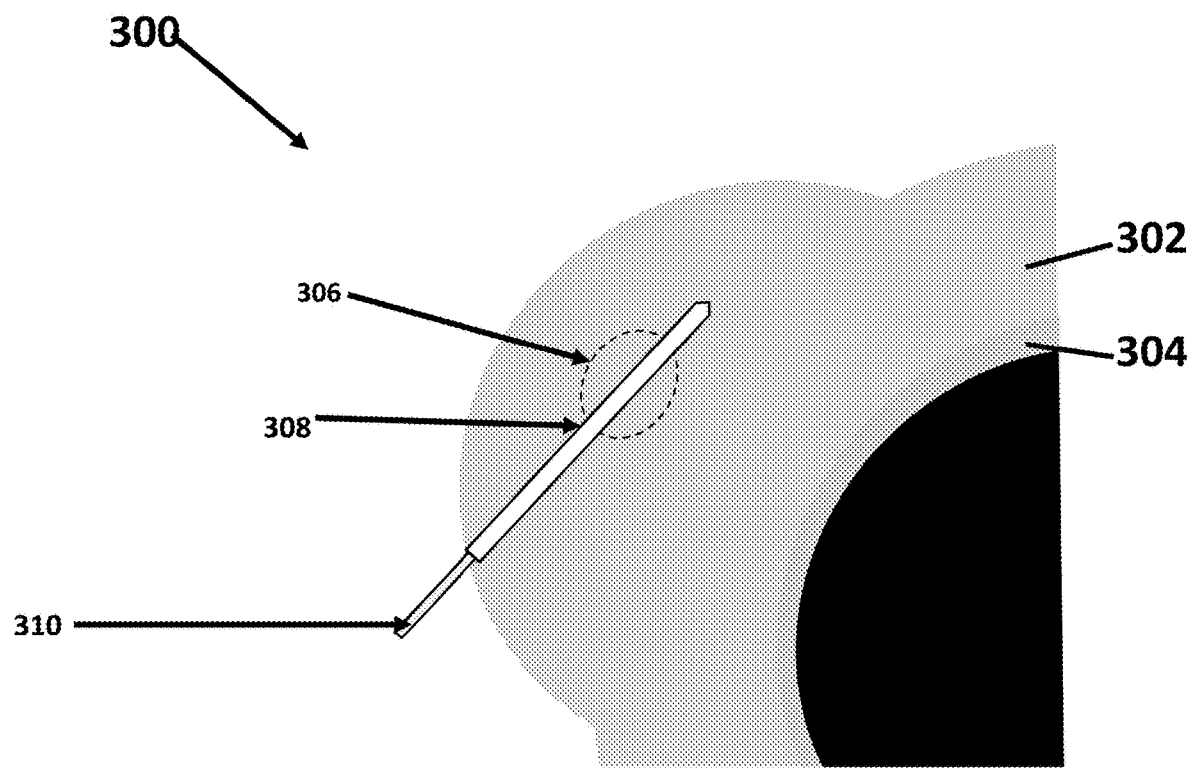
FIG. 4 illustrates a view of a breast with the implanted locator (needle guidance device) and a fiducial needle.

FIG. 3 shows a treatment site 306 (surgical cavity in this example) in a breast 302 against a chest wall 304 (after the tumor has been surgically removed in this example) with a locator 100 (needed guidance device 308) having been implanted into the surgical cavity of the breast tissue and possibly anchored using the anchoring feature as described above. FIG. 4 shows the breast tissue 302 with the implanted locator 308 in the treatment site 306 in which a fiducial needle 310 is inserted through the locator 308 into the breast tissue and the treatment site 306 (which is a surgical cavity in this example).

Figure 5:
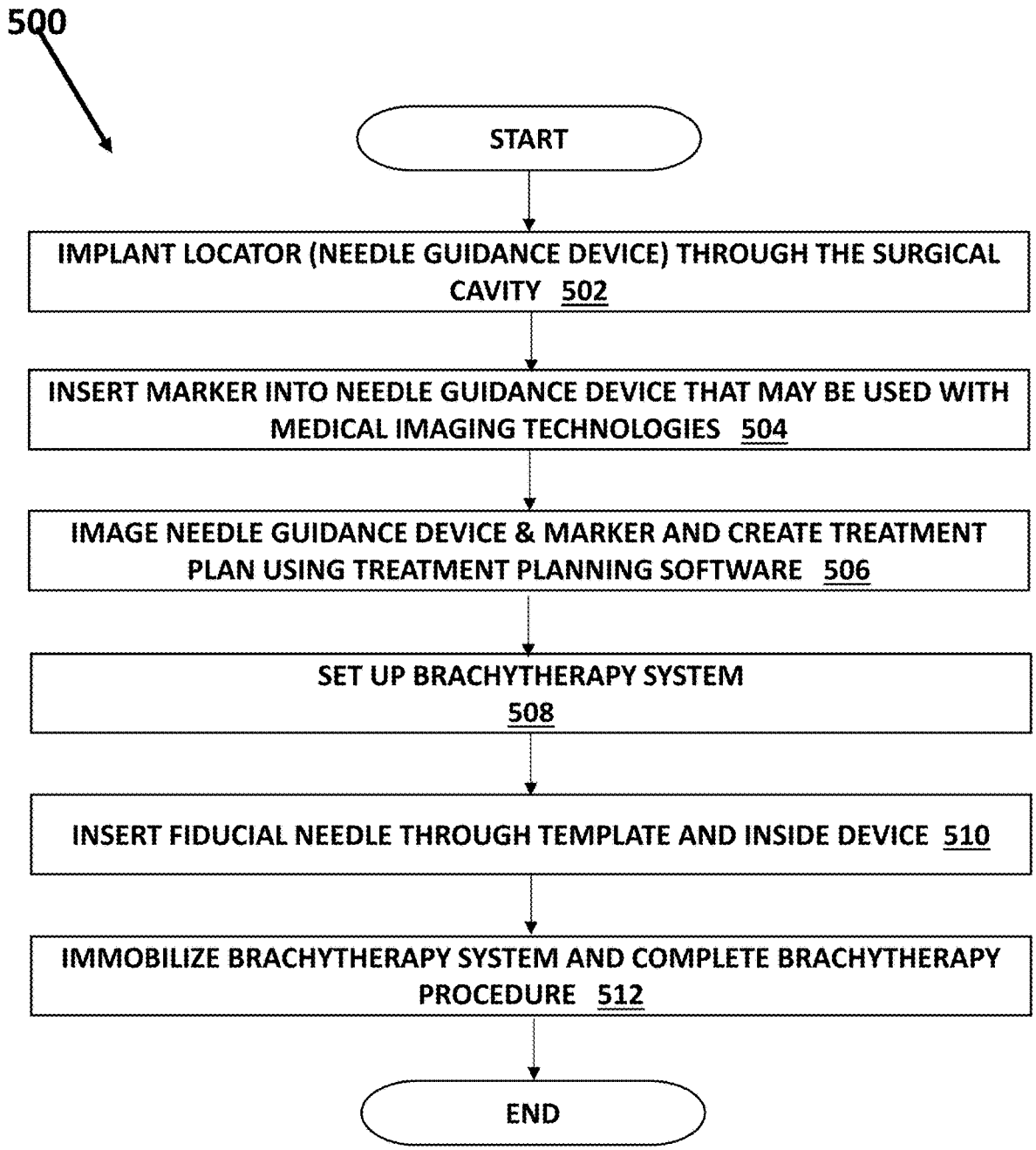
FIG. 5 illustrates a method for brachytherapy using the locator (needle guidance device) with a brachytherapy system.

FIG. 5 illustrates an example of a method 500 for brachytherapy using the locator disclosed herein for a brachytherapy treatment, such as placing radioactive seeds in breast tissue after surgery to kill cancer cells left behind following the surgery. It should be understood that the brachytherapy treatment can be performed to other tissues in which it is desirable to be able to implant radioactive seeds/sources into a treatment site.

In the example breast brachytherapy method, at the time of breast conservation surgery, the locator is a cannula that is placed percutaneously at the bottom of the cavity (502). The clinician can suture the cannula in the distal and proximal ends of the cavity to prevent migration. Then, a CT-visible marker is placed inside the cannula (504). With the visible marker, treatment planning is done (506) using treatment planning software, the cannula and CT-visible marker as reference points. The locator may have a feature that is visible using medical imaging that can be used by software for treatment planning (the feature can be radioopaque materials, sensors, or using it with other accessories like CT markers that can be picked up by imaging software which is imported into treatment planning software). One or more sets of characteristics of the locator, such as depth, angle and position, may be used by the treatment planning software to determine, for example, the planned insertion of the brachytherapy needle. The CT-visible marker is removed after the plan. The treatment planning determines, for example, the precise location of each radioactive seed/source being implanted into the breast tissue for the particular patient using the locator to precisely position each radioactive source.

On the day of the implantation, the template of the brachytherapy system is set up (508) that involves placing the patient on the OR table, adjusting the position of the template until it is appropriately adjacent to the treatment site and locking the template into position with the position fixed relative to the OR table and the treatment site. One end of the fiducial needle is placed through a fiducial needle hole of the template (510). The other end of the fiducial needle is inside the cannula. After the system is immobilized (with the fiducial needle being locked relative to the template in a well known manner), the radioactive sources are implanted (512). Once the implantation of the radioactive sources is completed, the method is completed.

The fiducial support device may be a device that is installed into the treatment site of the patient to support a brachytherapy treatment. The fiducial support device may be, for example, one or more of a needle that is solid or hollow, a post that is solid or hollow, a cannula, a guidewire, a catheter and/or a fiducial marker. The fiducial support device may stabilize the tissue around the treatment site. The fiducial support device can be used to orient a brachytherapy system in the various ways, such as, for example, the fiducial support device attaches to a brachytherapy template that then is used to precisely position the radioactive sources/seeds into the treatment site or the fiducial support device is a reference point.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include an/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims

What is claimed is:

1. A method for locating a brachytherapy needle, the method comprising:
    providing a locator device having a body portion with a distal end and a proximal end, an anchoring feature at the distal end of the body portion that is capable of anchoring the locator device into tissue and a plurality of markers along the length of the body portion wherein each marker indicates a depth of the locator device when it is installed into a treatment site;
    inserting the locator device into a treatment region in the tissue;
    anchoring, by the anchoring feature of the locator device, the locator device at the treatment region; and
    later inserting, using the locator device, a fiducial brachytherapy needle into the treatment region.

2. A brachytherapy treatment method using needle location, the method comprising:
    installing a locator device into a treatment region in a tissue;
    anchoring the locator device at the treatment region;
    using a set of characteristics of the locator device in a treatment planning software to generate a treatment plan;
    inserting, according to the treatment plan, a fiducial brachytherapy device into the treatment region using the locator device;
    placing one or more radioactive seeds into the treatment region; and
    attaching a brachytherapy template and wherein inserting the brachytherapy device further comprises inserting the brachytherapy device through the brachytherapy template into the treatment region.

3. The method of claim 2, wherein the brachytherapy device further comprises a brachytherapy fiducial needle.

4. A brachytherapy treatment method using needle location, the method comprising:
    installing a locator device into a treatment region in a tissue, wherein installing the locator device further comprises penetrating the tissue using a sharpened tip at a distal end of the locator device;
    anchoring the locator device at the treatment region;
    using a set of characteristics of the locator device in a treatment planning software to generate a treatment plan;
    inserting, according to the treatment plan, a fiducial brachytherapy device into the treatment region using the locator device; and
    placing one or more radioactive seeds into the treatment region.

5. A brachytherapy treatment method using needle location, the method comprising:
    installing a locator device into a treatment region in a tissue;
    anchoring the locator device at the treatment region, wherein anchoring the locator device further comprises suturing the locator device once installed into the treatment region;
    using a set of characteristics of the locator device in a treatment planning software to generate a treatment plan;
    inserting, according to the treatment plan, a fiducial brachytherapy device into the treatment region using the locator device;
    placing one or more radioactive seeds into the treatment region; and
    attaching a brachytherapy template and wherein inserting the brachytherapy device further comprises inserting the brachytherapy device through the brachytherapy template into the treatment region.

6. A brachytherapy treatment method using needle location, the method comprising:
    installing a locator device into a treatment region in a tissue;
    anchoring the locator device at the treatment region, wherein anchoring the locator device further comprises deploying one or more hooks once installed into the treatment region;
    using a set of characteristics of the locator device in a treatment planning software to generate a treatment plan;
    inserting, according to the treatment plan, a fiducial brachytherapy device into the treatment region using the locator device;

placing one or more radioactive seeds into the treatment region; and attaching a brachytherapy template and wherein inserting the brachytherapy device further comprises inserting the brachytherapy device through the brachytherapy template into the treatment region.

7. A brachytherapy treatment method using needle location, the method comprising:

installing a locator device into a treatment region in a tissue;

anchoring the locator device at the treatment region;

using a set of characteristics of the locator device in a treatment planning software to generate a treatment plan;

inserting, according to the treatment plan, a fiducial brachytherapy device into the treatment region using the locator device; and placing one or more radioactive seeds into the treatment region, wherein placing one or more radioactive seeds into the treatment region further comprises placing the one or more radioactive seeds into a lumpectomy cavity in breast tissue.

\* \* \* \* \*